United States Patent

Soukal

[11] Patent Number: 5,923,724
[45] Date of Patent: Jul. 13, 1999

[54] MEDICAL X-RAY DIAGNOSTIC INSTALLATION AND METHOD FOR OPERATING SAME

[75] Inventor: Peter Soukal, Schwarzenbruck, Germany

[73] Assignee: Siemens Aktiengesellschaft, Munich, Germany

[21] Appl. No.: 09/017,340

[22] Filed: Feb. 2, 1998

[30] Foreign Application Priority Data

Feb. 10, 1997 [DE] Germany ............................ 197 05 035

[51] Int. Cl.$^6$ ...................................................... G21K 3/00
[52] U.S. Cl. ................................................ 378/156; 378/98.7
[58] Field of Search ................................. 378/158, 156, 378/98, 99, 118, 98.7, 159; 250/370.09

[56] References Cited

U.S. PATENT DOCUMENTS

| | | | |
|---|---|---|---|
| 4,497,062 | 1/1985 | Mistretta et al. ........................ | 378/158 |
| 5,663,998 | 9/1997 | Suzuki et al. .............................. | 378/62 |
| 5,680,435 | 10/1997 | Seissl et al. ............................. | 378/156 |

FOREIGN PATENT DOCUMENTS

WO 84/04878 12/1984 WIPO .

*Primary Examiner*—David P. Porta
*Assistant Examiner*—Michael Schwartz
*Attorney, Agent, or Firm*—Hill & Simpson

[57] ABSTRACT

In a medical X-ray diagnostic installation and a method for operating same, an X-ray source has a filter means optionally introducible into its beam path and emits X-rays which strike a detector having individual pixel elements and which generates image signals pixel-by-pixel dependent on the received radiation. The detector is followed by a signal processing chain which includes processing meansfor image generation and output, first and only image exposure of the examination subject initially ensues without the filter means introduced into the beam path, after which the image signals obtained from one or more picture element regions of the received image are processed pixel-by-pixel for generating a calculated image corresponding to the image of those regions which would be obtained with the filter means in the beam path, using signals which identify a position of the filter means in the beam path. The processed signals are combined with the unprocessed signals for the remainder of the original image to produce a calculated image, which is supplied as an output for display. The production of a second, actual exposure employing X-rays with the filter means in the beam path is thus avoided, thereby saving time and reducing the patient's overall X-ray dose.

19 Claims, 1 Drawing Sheet

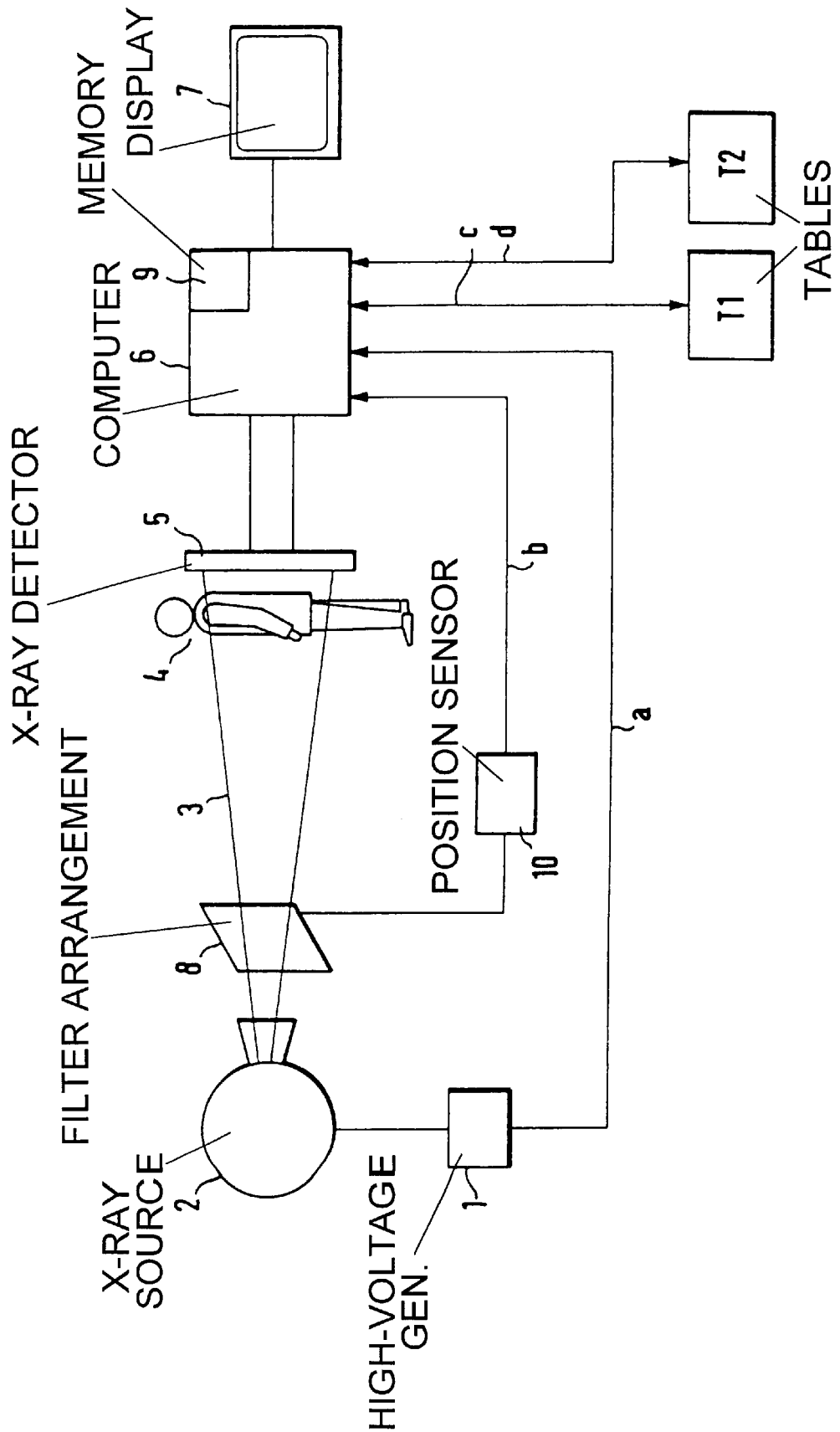

MEDICAL X-RAY DIAGNOSTIC INSTALLATION AND METHOD FOR OPERATING SAME

BACKGROUND OF THE INVENTION

1. Field of the Invention

The present invention is directed to a medical X-ray diagnostics installation and a method for operating same, the installation being of the type having an X-ray source, with a filter optionally introducible into the beam path, and a detector that receives the X-radiation having individual picture elements and which supplies image signals pixel-by-pixel dependent on the received radiation, and a computer for image generation and output.

2. Description of the Prior Art

The exposure of an X-ray image usually ensues by first making a fluoroscopic exposure of the examination subject in order to obtain information in view of, among other things, the illumination distribution of the X-ray exposure. If it turns out that regions of excessively great illumination exist within the exposure, which can be the case due to subject locations of different density and thus different absorbency, then these can be largely eliminated by introducing a corresponding filter, for example a wedge filter or a graduated filter, into the beam path. The radiation dose applied to the subject in this region, and thus the dose ultimately reaching the detector as well thus being reduced, i.e. filtered. The positioning of the filter, for example semi-transparent diaphragm lamellae, is thereby manually carried out by the operator, who inserts the filter into the beam path in conformity with the knowledge about the over-irradiated regions. A further fluoroscopic exposure is required in order to know the correct position of the filter and its filtering effect and in order to decide whether the positioning is adequate, i.e. another radiation image must be registered. This, however, is extremely disadvantageous, particularly since the patient must be exposed to a radiation dose again. Further, the implementation of the second fluoroscopic exposure is disadvantageous for the overall examination sequence itself, particularly in view of time.

PCT Application 84/04878 A1 discloses a method as well as an apparatus for the production of filters that are subsequently introduced into the beam path. The production ensues such that a filter is arranged in the beam path in the framework of a first fluoroscopic exposure. Dependent on the transmission signals identified with a pick-up unit, a filter material is then deposited on the filter with an appropriate device. After the production of this filter, it is subsequently placed into the beam path, after which the actual second exposure ensues.

SUMMARY OF THE INVENTION

An object of the present invention is to provide a method and apparatus which, given adequate knowledge of the effect of the filter on a radiation exposure, enable a minimization of the applied radiation dose and an acceleration of the examination sequence.

This object is achieved in a method and apparatus of the invention wherein a first and only image exposure of the examination subject initially ensues without a filter introduced into the beam path. After this single exposure, information identifying a position of the filter in the beam path is supplied to a computer and image signals for those pixels which will be covered when the filter is introduced into the beam path are processed pixel-by-pixel in the computer and a calculated image is generated from these processed signals and from the remainder of the image signals in the single exposure, which will not be effected by the introduction of the filter into the beam path. The calculated image thus represents the same type of image which is produced in the aforementioned conventional systems, with the filter introduced into the beam path, but there is no necessity to again activate the x-ray source in order to produce the calculated image.

With particular advantage, thus, the inventive method creates the possibility of pre-calculating the image which would be obtained if the second conventional fluoroscopic exposure were made, i.e. it is possible for the physician to obtain knowledge about the position and the effect of the filter which will be introduced into the beam path, without actually implementing a second radiation exposure. In this way, only the implementation of a single (i.e. the first) fluoroscopic exposure is required; a second exposure is no longer required for obtaining knowledge of the filtering effect. The X-ray dose applied to the patient is thus advantageously considerably reduced and the examination sequence is significantly accelerated.

It has proven especially expedient from a processing-oriented point of view to process the gray scale values of the respective picture elements in the framework of the overall signal processing. The processing expediently ensues dependent on specific filter data which may relate to one or more parameters of one or more apparatus components, the number of filters, the geometry of the filter and/or the absorption properties of the filter. The parameters may be normed (normalized) to a reference material thickness dependent, for example, on the X-ray tube voltage. All specific filter data ultimately influence the nature of the filtering as well as the image regions covered by the filter are employed and within the signal processing so that knowledge and incorporation of these influences in the processing leads to adequately exact and diagnostically relevant calculated images. In addition to the specific filter data, the processing can ensue dependent on specific parameters of at least one apparatus component, the generator-side tube operating voltage with which the first radiation image was exposed being particularly relevant. Further, taking specific parameters of all image-generating and output components into consideration is meaningful since these also ultimately enter into the image shown at the respective output means, i.e. processing-specific parameters are to be taken into consideration. The voltage of the X-ray source selected in the framework of the first image exposure and/or specific parameters of the components following the X-ray apparatus can be inventively employed as such specific parameters. Expediently, all component-specific or filter specific parameters are stored in the form of a table, from which the respective parameters are selected for a given situation.

From a processing-oriented point of view, it has proven expedient in the framework of the signal processing, for example of the gray scale values, to first determine correction value based on the signal obtained in the framework of the first exposure and to subsequently computationally operated on this value with the obtained signal, particularly subtracted therefrom, for generating the signal employed in the calculated image. For example in the case of the gray scale value processing, a gray scale attenuation value is identified that is then subtracted from the actual initial value in order to obtain the calculated image value. The correction value itself can be inventively determined by computational operation, particularly multiplication, of an attenuation value determined dependent on the specific filter means data and an attenuation value determined dependent on the apparatus component, the specific attenuation value for the apparatus component is preferably a multiplication coefficient.

As already set forth, a pre-calculation of an anticipated X-ray image is possible with the inventive method. In an embodiment of the inventive method and apparatus the position of the filter is continuously acquired, and the calculated image is generated dependent on the position or on a change in position. It is thus possible in this embodiment to already define the region within which the processing should ensue by automatic acquisition of the filter position, so that completely automatic operation is achieved. An "on-line" operation that leads to a continuous generation and output of the calculated image can also be enabled with this embodiment for generating a calculated image given a change in the filter position. When the operator readjusts and displaces the filter, for example after output of a first calculated image, then the change in position of the filter is automatically acquired according to this inventive embodiment and a second calculated image is subsequently produced so that the operator can immediately see the effect of the manual modification, for example at the monitor. An "on-line" simulation of the X-ray image is thus possible.

The inventive method X-ray diagnostics installation for implementation of the above-described method includes an X-ray source, with a filter optionally introducible into its beam path, a detector that receives the X-radiation, having individual picture elements and which produces image signals pixel-by-pixel dependent on the received radiation, and a computer for image generation and output of the image to an output device, such as a display. The computer generates the aforementioned calculated image that corresponds to an image as would be expected if a further image exposure with the filter introduced in the beam path were made. The calculated image is based on the signals obtained without the filter in a first (and only) image exposure of the examination subject.

An arrangement can be provided for acquiring the position of the filter, with the computer generating the calculated image dependent on this position data. The computer can undertake generation of the calculated image dependent on specific filter data, particularly the number of filters, the geometry of the filter, the material of the filter and/or the absorption properties of the filter. Moreover, the computer can generate the calculated image dependent on specific parameters of at least one apparatus component, particularly the voltage of the X-ray source, selected in the framework of the first image exposure, and/or dependent on specific parameters of the components following the detector. In this way, it is possible to virtually take all parameters entering into the attenuation and processing of the respective signals into consideration in the generation of the calculated image.

In an embodiment of the invention the acquisition of the position of the filter can be done continuously, and that the computer then can generate the calculated image dependent on a change of the position data in order to enable a continuous display of the calculated image, and thus a tracking of the result which occurs due to a positional change of the filter. Since a computational transition from the signals of the first image exposure ensues to the calculated signals, a modification of the filter position in this "on-line" image generating mode would result in the original signals (before the change in filter position) being lost. Therefore, a memory for the signals obtained in the first image exposure is provided in order to be able to have been able to retrieve these signals in the calculation of a further calculated image. This allows the original signals (for the regions that are no longer covered by the filter in its changed position) to be used in the new calculated image. These original signals would otherwise have to be generated by a back-calculation.

DESCRIPTION OF THE DRAWINGS

The single FIGURE is a block diagram of an X-ray diagnostic installation constructed and operating in accordance with the principles of the present invention.

DESCRIPTION OF THE PREFERRED EMBODIMENTS

The FIGURE shows an inventive X-ray diagnostic installation for the implementation of the inventive method. An X-ray source 2 driven via a high-voltage generator 1 and emits an X-ray beam 3 that penetrates a subject 4 and strikes a detector 5, for example a matrix detector or an image intensifier. The detector 5 is followed by a signal processing chain including a computer 6 for image generation and output and a display 7, for example a monitor. A filter arrangement 8 that effect a pre-filtering of the X-rays is arranged in the X-ray beam of the X-ray source 2. The filter arrangement 8 can, for example, be one or more wedge filters. A number of such filters can be provided in the filter arrangement 8 in order to allow an optimally exact matching to the current conditions.

For implementing the inventive method, the X-ray diagnostic installation first is operated to produce a fluoroscopic exposure, the subject 4 being transirradiated with low-dose X-radiation during the course thereof in order to obtain information about the positioning of the subject 4 and about the exposure quality on the basis of the exposure. The X-rays attenuated by the subject 4 strike the detector 5 and are converted therein into radiation-dependent signals that are supplied to the computer 6. This computer 6 contains (or has access to) a memory 9 in which the signals obtained during the course of the first exposure are stored. After processing the supplied signals in the computer 6, the fluoroscopic image is supplied as an output to the display 7.

With reference to the output fluoroscopic image, the operator can now determine whether there are over-exposure regions that are to be compensated with the filter arrangement 8. When this is the case, the filter arrangement 8 is placed into the beam path 3 dependent on the position of the over-exposure regions recognizable at the display 7. A position sensor 10 for recognizing the position of the filter arrangement 8 are allocated to the filter arrangement 8, the position of the filter arrangement 8 relative to the detector 7, and thus relative to the image visible at the display 7, being automatically determined therewith. The introduction of the filter arrangement 8 thereby occurs without the production of X-rays. In order to then generate the fluoroscopic image which would (will) exist after introduction of the filter arrangement 8, a number of processing parameters are supplied to the computer 6, particularly the operating parameters of the high-voltage generator 1 that serve as criterion for the quality of the emitted X-radiation. Further, the position data of the filter arrangement 8 identified by the position sensor 10 are supplied to the computer 6, (arrow b).

Two tables T1 and T2 that are accessible by the computer 6 (arrows c, d) are also allocated to the computer 6. The table T1 contains absorption values of the filters of the filter arrangement 8 dependent on the operating voltage of the X-ray source 2. This makes it possible to determine the appertaining absorption value for every source operating voltage. This absorption value is specific to each filter, i.e. it takes into account the required filter data such as, for example, the material of the filter, the geometry of the filter, etc. By contrast, correction values, that serve for taking signal variations and fluctuations which occur within the computer 6 into consideration, are stored in table T2. Dependent on the nature of the computer 6 and of the display 7 employed, of course, different influences on the signal processing occur that in turn influence the respective signals which are produced.

The calculation of the expected image with the filter arrangement in the X-ray beam ensues pixel-by-pixel. Only the picture elements that are "affected" by the filter arrangement 8, i.e. whose signal would change if a further fluoroscopic exposure were made with the filter arrangement 8 in the beam path 3, are taken into consideration in the processing. These picture elements are known from the knowledge of the position of the filter arrangement 8 obtained from the position sensor 10. These picture elements are now calculated as follows in terms of their gray scale values, this calculation ensuing for every individual picture element:

First, the calculation of the filter attenuation $S_{Image}$ ensues in two steps:

1. Attenuation of the detector entry dose $S_{Dose}$:

$S_{Dose}$=value from absorption table T1 dependent on the source voltage.

2. Attenuation of the gray scale value $S_{Image}$:

$S_{Image}=S_{Dose}\times$correction value from table T2.

The image attenuation $S_{Image}$ obtained in this way is subsequently subtracted from the respective gray scale value in order to obtain the calculated gray scale value:

$$G_{Calculate}=G_{Transirradiation}-S_{Image}$$

The calculation for the next picture element ensues after determination of the calculated gray scale value $G_{Calculate}$ until all picture elements in the overexposed region are processed. Subsequently, the computational gray scale values are operated on the other, non-processed gray scale values of the regions that are not overexposed (and thus not covered by the filter arrangement 8) in order to obtain the overall calculated image, which is subsequently supplied as an output. With reference thereto, the operator can then recognize and if necessary correct the pre-filtering which ensues due to the manual introduction of the filter arrangement 8. When such a correction is required, then the filter arrangement 8 is correspondingly shifted, and a new generation of the calculated image ensues due to the renewed position acquisition. In this case, the computer 6 accesses the first fluoroscopic image signals stored in the memory 9 and produces the new calculated image based thereon.

Although various minor modifications might be suggested by those skilled in the art, it should be understood that I wish to embody within the scope of the patent warranted hereon all such modifications as reasonably and properly come with the scope of my contribution to the art.

I claim as my invention:

1. A method for operating a medical X-ray diagnostic installation having an X-ray source which emits an X-ray beam in a beam path, filter means introducible into said beam path, a detector, comprised of a plurality of pixels, which receives said X-ray beam and which emits pixel-by-pixel image signals dependent on incident X-rays, and means for processing the image signals, said method comprising the steps of:

activating said X-ray source to emit said X-ray beam in a first image exposure without said filter means introduced into said beam path, said detector producing image signals during said first exposure;

defining one or more pixel areas of said detector identified by the position of said filter means relative to said detector, when said filter means is placed in said beam path for a second exposure;

processing the said produced pixel-by-pixel image signals of said one or more pixel areas of said detector which will be effected by said filter means in said beam path without re-activating said X-ray source; and generating a calculated image from the said processed image signals for said pixels effected by said filter means and the image signals of a remainder of said pixels which are unaffected by said filter means.

2. A method as claimed in claim 1 wherein the step of processing said signals produced in said first image exposure comprises processing gray scale values of said pixels effected by said filter means in said beam path.

3. A method as claimed in claim 1 comprising the additional steps of obtaining filter data identifying at least one parameter of said filter means and employing said filter data in processing said image signals for said pixels effected by said filter means.

4. A method as claimed in claim 3 comprising the step of selecting said filter data from the group consisting of a number of filter means, a geometry of said filter means, a material of said filter means, and absorption properties of said filter.

5. A method as claimed in claim 3 wherein said X-ray source, said detector and said means for processing comprise apparatus components, and comprising the additional steps of:

obtaining an apparatus component-specific parameter of at least one of said apparatus components; and employing said at least one apparatus-specific component in the processing of said image signals of said pixels effected by said filter means.

6. A method as claimed in claim 5 wherein said apparatus-specific parameter comprises a voltage of said X-ray source employed during said first image exposure.

7. A method as claimed in claim 1 wherein the step of processing said image signals of said pixels effected by said filter means comprises the steps of:

for each pixel, calculating a correction value from the image signal obtained during said first image exposure;

using said correction value, computationally operating on the image signal from which said correction value was obtained to produce a computational result; and for each pixel, using said computational result in said calculated image.

8. A method as claimed in claim 7 wherein the step of computationally operating on said image signal comprises subtracting said correction value from the image signal from which said correction value was obtained.

9. A method as claimed in claim 7 wherein said X-ray source, said detector and said means for processing comprise apparatus components, and comprising the additional steps of:

obtaining filter-specific data identifying a parameter associated with said filter means;

obtaining apparatus component-specific data identifying a parameter of one of said apparatus components;

calculating a first attenuation value dependent on said filter-specific data;

calculating a second attenuation value dependent on said apparatus-specific data; and calculating said correction value by multiplying said first attenuation value with said second attenuation value.

10. A method as claimed in claim 9 wherein said second attenuation value comprises a multiplication coefficient.

11. A method as claimed in claim 1 wherein the step of identifying the position of said filter means comprises continuously identifying the position of said filter and producing said calculated image dependent on a change in position of said filter means.

12. An X-ray diagnostic installation comprising:
an X-ray source which emits X-rays along a beam path;
filter means selectively introducible into said beam path;
an X-ray detector on which said X-ray are incident, said X-ray detector comprising a plurality of pixels and generating image signals pixel-by-pixel dependent on X-rays incident on the respective pixels;
processing means for processing said image signals to produce a visible image;
means for activating said X-ray source in a first exposure, said detector producing image signals during said first exposure; and
said processing means comprising means for processing image signals for pixels of said detector effected by said filter means in said beam path for producing a calculated image comprising the process image data signals and the image signals from a remainder of said pixels not effected by said filter means in said beam path.

13. An X-ray diagnostic installation as claimed in claim 12 comprising position signal source means for producing position signals identifying a position of said filter means when introduced in said beam path, wherein said image signals for pixels of said detector effected by said filter means in said beam path are processed dependent on said position signals by said means comprised in said processing means.

14. An X-ray diagnostic installation as claimed in claim 13 wherein said position signal source means comprises a position sensor which generates signals identifying an actual position of said filter means in said beam path.

15. An X-ray diagnostic installation as claimed in claim 13 wherein said means for processing comprises means for processing said image signals of said pixels effected by said filter means and said beam path dependent on filter-specific data selected from the group consisting of a number of filter means, a geometry of said filter means, a material of said filter means, and absorption properties of said filter means.

16. An X-ray diagnostic installation as claimed in claim 15 wherein said means for processing comprises means for processing said image signals of said pixels effected by said filter means in said beam path using a component-specific parameter selected from the group consisting of parameters associated with said X-ray source, parameters associated with said detector and parameters associated with said means for processing.

17. An X-ray diagnostic installation as claimed in claim 15 wherein said component-specific parameter comprises a voltage of said X-ray source employed for producing said first exposure.

18. An X-ray diagnostic installation as claimed in claim 12 wherein said position signal source means comprises means for continuously acquiring an actual position of said filter means in said beam path, and wherein said means for processing comprises means for producing said calculated image dependent on a change of position of said filter means.

19. An X-ray diagnostic installation as claimed in claim 18 further comprising memory means for storing said image signals obtained in said first exposure.

* * * * *